United States Patent
Tikhonski et al.

(10) Patent No.: US 9,111,738 B2
(45) Date of Patent: Aug. 18, 2015

(54) NONRADIOACTIVE IONIZATION SOURCE DRIVER

(71) Applicant: APPLIED NANOTECH HOLDINGS, INC., Austin, TX (US)

(72) Inventors: Alexei Tikhonski, Austin, TX (US); Leif Thuesen, Austin, TX (US)

(73) Assignee: PEN Inc., Deerfield Beach, FL (US)

( * ) Notice: Subject to any disclaimer, the term of this patent is extended or adjusted under 35 U.S.C. 154(b) by 0 days.

(21) Appl. No.: 14/355,296

(22) PCT Filed: Jan. 17, 2013

(86) PCT No.: PCT/US2013/021853
§ 371 (c)(1),
(2) Date: Apr. 30, 2014

(87) PCT Pub. No.: WO2013/109699
PCT Pub. Date: Jul. 25, 2013

(65) Prior Publication Data
US 2014/0291506 A1 Oct. 2, 2014

Related U.S. Application Data (60) Provisional application No. 61/587,352, filed on Jan. 17, 2012, provisional application No. 61/618,947, filed on Apr. 2, 2012.

(51) Int. Cl.
| | |
|---|---|
| *G21K 5/00* | (2006.01) |
| *H01J 49/10* | (2006.01) |
| *H05H 1/24* | (2006.01) |
| *H01J 49/02* | (2006.01) |
| *G01N 27/62* | (2006.01) |

(52) U.S. Cl.
CPC .............. *H01J 49/10* (2013.01); *H01J 49/022* (2013.01); *H05H 1/2406* (2013.01); *G01N 27/624* (2013.01); *H05H 2001/2412* (2013.01); *H05H 2245/121* (2013.01)

(58) Field of Classification Search
USPC .......... 250/423 R, 424, 425, 426, 427, 423 F, 250/423 P, 280, 281, 288
See application file for complete search history.

(56) References Cited

U.S. PATENT DOCUMENTS

| | | | |
|---|---|---|---|
| 5,565,114 A | 10/1996 | Saito et al. | |
| 2002/0185593 A1 | 12/2002 | Doring | |
| 2003/0070913 A1* | 4/2003 | Miller et al. | ............... 204/192.1 |
| 2004/0094704 A1 | 5/2004 | Miller et al. | |
| 2007/0083127 A1* | 4/2007 | Merrick et al. | ............... 600/532 |
| 2008/0156978 A1* | 7/2008 | Shvartsburg et al. | ......... 250/282 |

(Continued)

OTHER PUBLICATIONS

The International Bureau of WIPO; International Preliminary Report on Patentability for PCT/US2013/021853; Jul. 31, 2014.

(Continued)

*Primary Examiner* — Nicole Ippolito
(74) *Attorney, Agent, or Firm* — Kelly Kordzik; Matheson Keys & Kordzik PLLC (57) ABSTRACT

System and method for operating an ionizer using a combination of amplitude modulation and pulse width modulation to control the plasma temperature and the type of ions needed for analytic equipment. Ion density can be controlled by the repetition rate. The ionizer may utilize a non-radioactive ionization source, and be coupled to a differential mobility spectroscopy (DMS) analyzer.

22 Claims, 8 Drawing Sheets

(56) References Cited

U.S. PATENT DOCUMENTS

| | | |
|---|---|---|
| 2008/0156981 A1 | 7/2008 | Miller et al. |
| 2011/0198511 A1* | 8/2011 | Graupera et al. ......... 250/396 R |
| 2011/0210242 A1 | 9/2011 | Bateman |

OTHER PUBLICATIONS

United States International Searching Authority; Written Opinion of the International Searching Authority for PCT/US2013/021853; Mar. 22 2013; Alexandria, VA; US.

* cited by examiner

NONRADIOACTIVE IONIZATION SOURCE DRIVER

This application claims priority to U.S. Provisional Patent Applications Ser. Nos. 61/587,352 and 61/618,947, which are hereby incorporated by reference herein.

TECHNICAL FIELD

The present invention relates in general to utilization of gas ionization for detection of chemical compounds, such as in air.

BACKGROUND INFORMATION

Ion Mobility Spectrometry ("IMS") for the detection of chemical warfare agents ("CWAs"), toxic industrial chemicals ("TICs"), drugs, and explosives is primarily based on gas ionization by radioactive sources (e.g., $^{63}$Ni, $^{241}$Am, and $^{3}$H), since these sources meet requirements of a portable device for field use: small sized and lightweight, good mechanical stability, and do not require any additional power. Furthermore, they are very reliable while displaying a good sensitivity with regard to the detection of quite a large number of compounds of interest. However, for well-known reasons (e.g., radiation safety, regulation, record keeping, disposal problems) there is a growing interest in replacing radioactive sources by alternative gas ionization techniques.

One type of ionization source is a dielectric barrier discharge as ionizer, which has two metal electrodes separated by an insulator. However, in this configuration, one of the electrodes is exposed to the gas being ionized, which can lead to electrode erosion and gas contamination.

DETAILED DESCRIPTION

Figure 6:
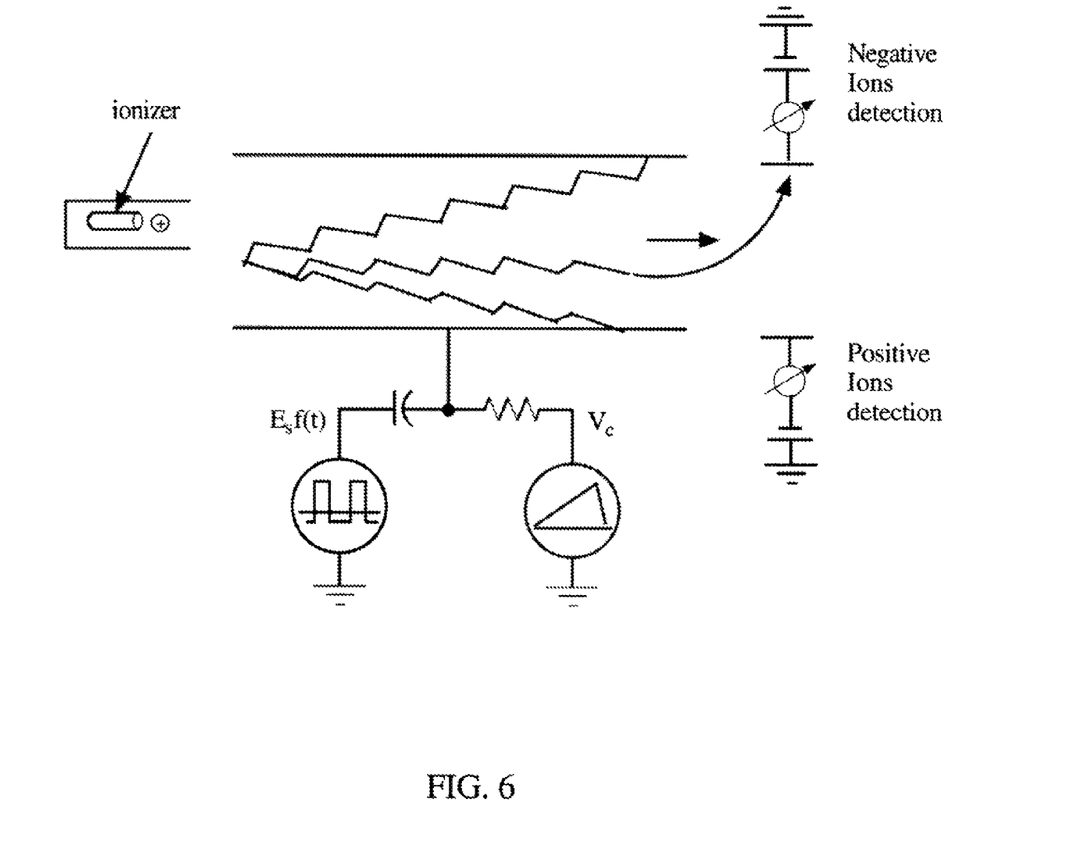
FIG. 6 illustrates a principle of operation of a DMS as an ion filter using the principles of ion mobility.

Embodiments of the present invention provide a nonradioactive ionization source that exhibits stability, low power consumption, and long lifetime to replace radioactive sources. The nonradioactive ionization source may be used in place of radioactive sources for instruments such as a differential mobility spectroscopy ("DMS") analyzer and other ion mobility spectrometers ("IMS"), such as a time of flight ion mobility spectrometer and field asymmetric ion mobility spectrometers. As illustrated in FIG. 6, a principal of operation of such a DMS has volatile organic compound ("VOC") analyte molecules ionized as they enter the DMS. The DMS is essentially an ion filter operating in a gas environment. In embodiments of the present invention, the gas environment is filtered and dried (de-humidified) air at near atmospheric pressure. As previously noted, the most common technique used to create gas ions is to place a radioactive source material (either beta emitter or alpha emitter) next to the gas flow. The inventors succeeded in developing an ion generator that does not utilize radioactive sources.

Figure 1A:
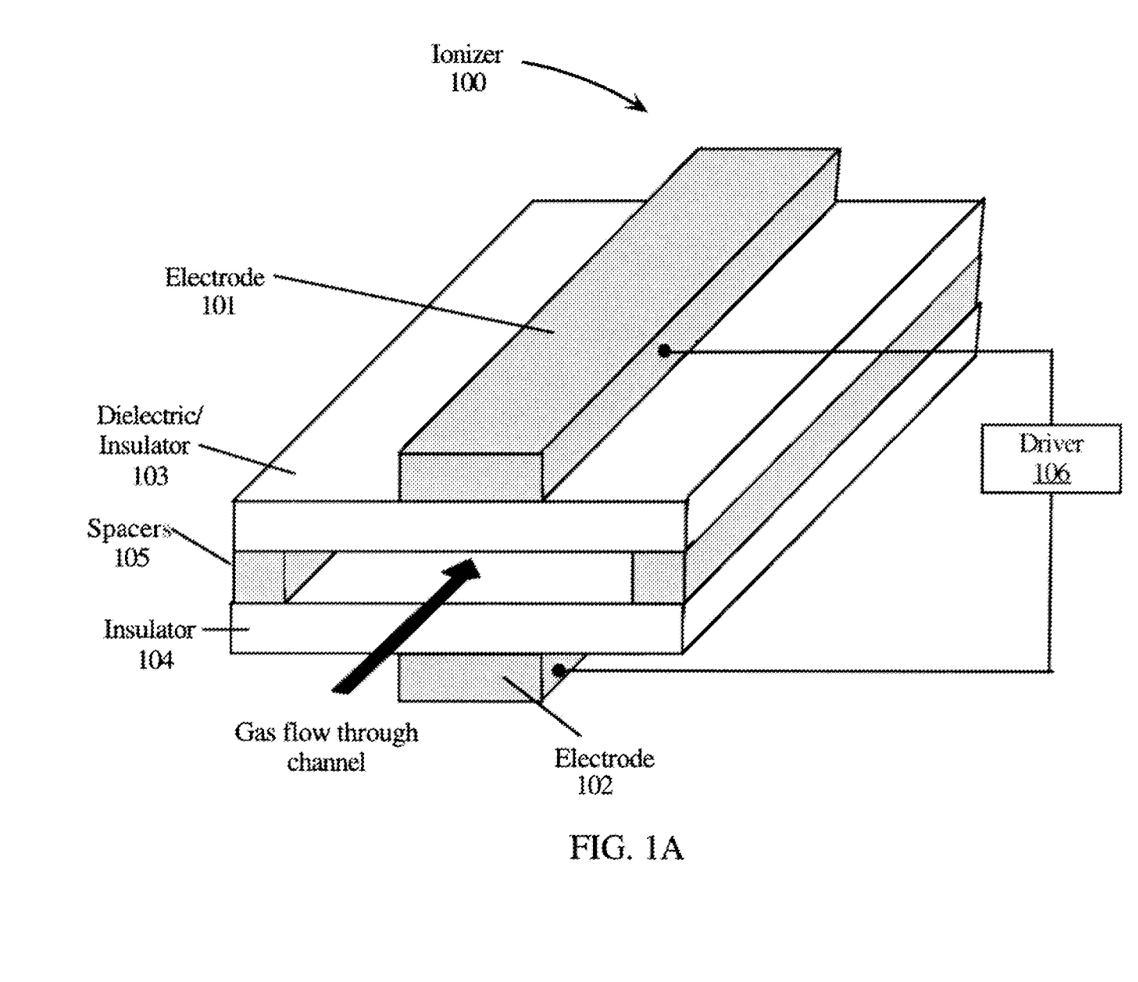
FIG. 1A illustrates a non-radioactive ionization source configured in accordance with embodiments of the present invention.
Figure 1B:
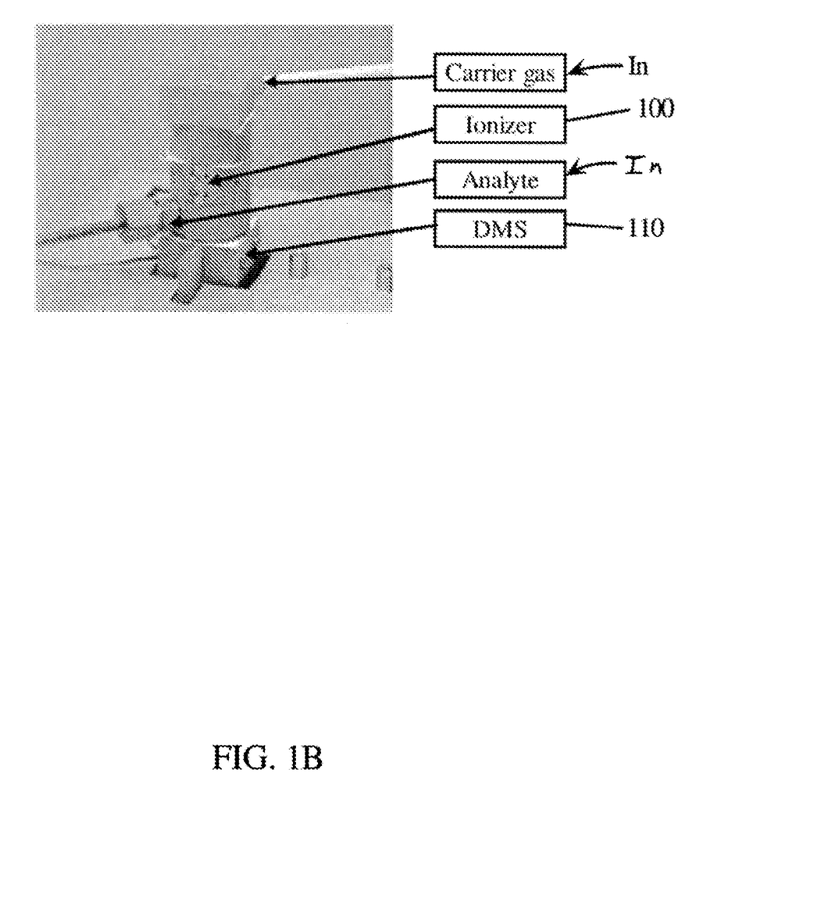
FIG. 1B shows a digital image of a differential mobility spectroscopy ("DMS") analyzer configured in accordance with embodiments of the present invention.

Referring to FIG. 1A, the radioactive gas ionization source is replaced with a non-radioactive gas ionization ("NRI") source 100. The NRI 100 may include plates comprising two parallel electrodes 101, 102 coated with a dielectric material 103, 104. The electrodes 101, 102 may be held apart by spacers 105 in a configuration in which the dielectric surfaces face each, other and allow gas to flow through the channel between them. In such a configuration, the metal electrodes 101, are not exposed to the gas or ions and thus are protected from plasma erosion. As shown in FIG. 1B, a DMS analyzer 110 may be coupled to the ionizer 100. The carrier gas flows into the assembly of FIG. 1B and through the ionizer 100, The carrier gas is ionized in the ionizer 100 and continues to flow through the assembly. Analyte is introduced into the ionized carrier gas where charge exchange occurs creating analyte ions. The mixture of carrier gas, carrier gas ions, analyte, and analyte ions then flows into the DMS 110 for analysis and thereafter the gas is exhausted.

To create ions, a plasma is generated between the plates by application of an alternating voltage ("AC") across the electrodes 101, 102, As a nonlimiting example, the peak voltage may be in a range of approximately 3 kV to 8 kV, With a larger gap between the plates, a higher voltage is needed: using a smaller gap allows lowering the peak voltage. Typically, this AC voltage is driven in a non-regulated manner, such as with a continuous waveform ("CW"), and the voltage is merely adjusted to a level where the plasma ignites. Using this method of driving the NRI, the plasma is difficult to keep stable and power consumption is poorly regulated. Furthermore, the non-regulated driving method also creates negative ions (e.g., nitrous oxide and other compounds) that are highly electronegative and thus do not easily share their charge with other compounds. Thus, a non-regulated NRI creates an ample number of negative ions, but these ions are effectively useless in that they do not result m ionization of the analyte compounds of interest. Moreover, if using a high power driver in air, a lot of ozone may he created.

To address such problems, a driving method and circuitry in accordance with embodiments of the present invention is disclosed herein to reduce power consumption and maintain stability of the plasma. A more regulated driver may be used to generate as soft plasma more useful for ion mobility, since it may be better to create ions that have low electronegativity (e.g., negative oxygen and water molecules such as $O_2^-$ and $H_2O^-$) that will share their charge with molecules and volatile organic compounds of interest in the sampled gas being characterized by the ion mobility tool.

By adjusting the gas flow and electrode dimensions, the ionization of the vas can be better controlled, To maintain a soft plasma, the gas should not be excited once it has already been ionized. By increasing the gas flow rate, ions pass out of the ionization region before a new voltage cycle is applied to the ionizer. A similar result may also achieved by shortening the electrode so that ions pass out of the ionization region before the new voltage cycle applies.

Figure 2:
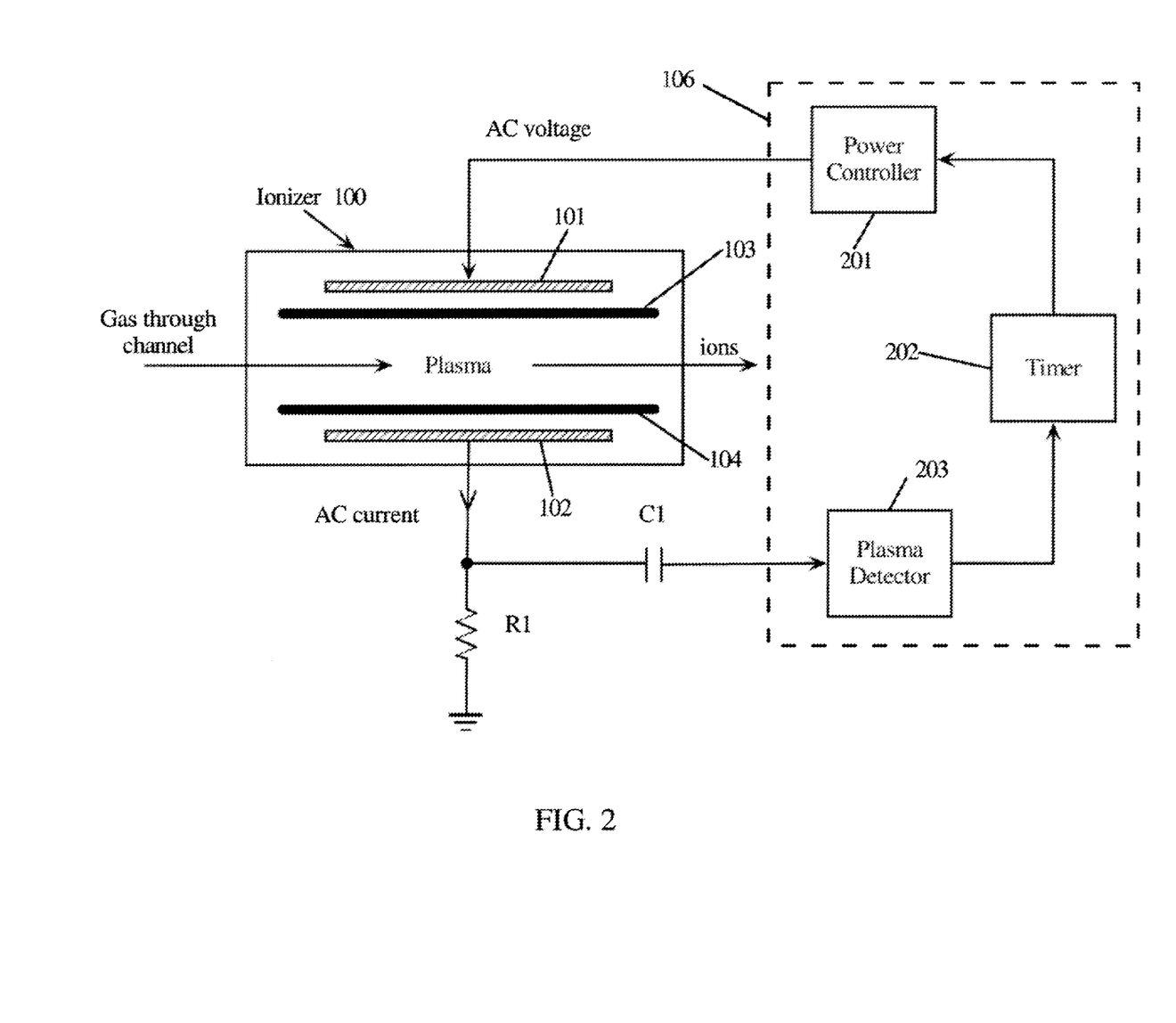
FIG. 2 illustrates a block diagram of an ionizer and driver configured in accordance with embodiments of the present invention.

Referring to FIG. 2, an ionization source driver in accordance with embodiments of the present invention comprises:

1. A power controller 201: Controls sinusoidal voltage (e.g., 0 to 8 kV (peak to peak) of frequencies from 300 to 500 kHz) applied, to the discharge electrodes 101, 102;

2. A timer 202: Switches (or, pulses) the power controller 201 ON and OFF in accordance to a predetermined pulse width modulated frequency (e.g., with a repetition rate from 0.5 to 3.0 KHz, and pulse width from 50 µS to 500 µS);

3. A plasma detector 203: Monitors current through the discharge electrodes 10 102 and generates a signal sent to the timer 202 when the plasma ignites in the ionizer 100.

In general, as previously noted, the plasma ignition process is very unstable. To ignite a plasma in the NRI 100, the AC voltage applied to the discharge electrodes 101, 102 may depend on humidity, gas pressure, gas flow rate, gas composition, insulator properties, NRI gap, and other factors. In order to produce the desired ions, the plasma should be as "cold" as possible (i.e., of a lower power). The higher the power of the plasma (i.e., a "hot" plasma.), the more $NO_x$ ions are created. $NO_x$ ions inhibit, ionization of the analyte ions being studied in an IMS system. Therefore, the power (AC voltage) applied to the discharge electrodes 101, 102 should be as low as possible, but yet sufficient to ignite the plasma. The high power makes the NRI ignition process even more unstable.

To stabilize the process and produce a stable stream of desired ions, the following method was developed and the device (ionization source driver) designed. The method turns the AC voltage ON according to a repetition rate set by a user (i.e., a predetermined pulse width modulated frequency), and then turns the AC voltage OFF when a plasma discharge is detected. This allows the gas to cool and prevents continuous, hotter ionization. The process may then be stabilized using pulse width modulation with feedback from a plasma discharge detector 203.

Figure 4:
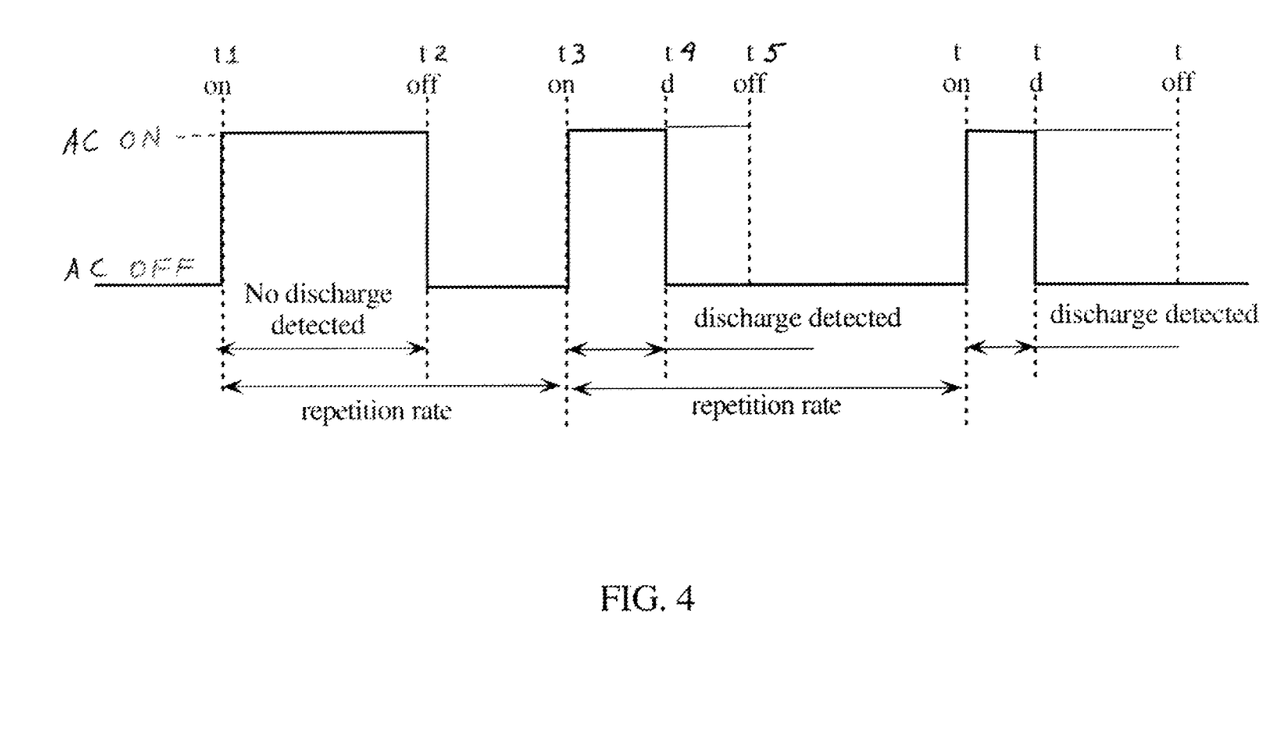
FIG. 4 illustrates a schematic of pulse operation showily, exemplary voltage pulse repetition rate.
Figure 5:
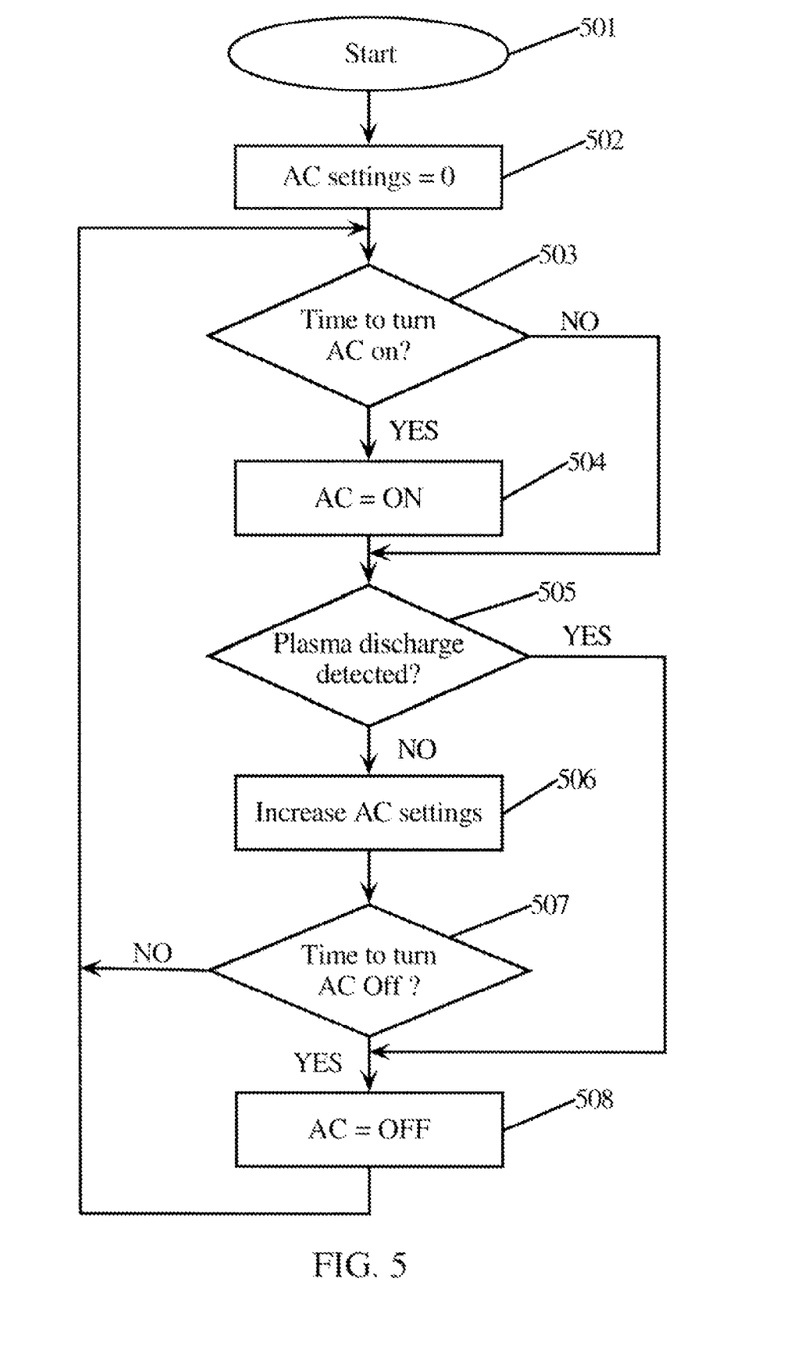
FIG. 5 illustrates a flow diagram of a stabilization process in accordance with embodiments of the present invention.

Refer next to the flow diagram illustrated in FIG. 5, FIG. 4 is a schematic of an exemplary AC voltage pulse operation, which operates as described below with respect to FIG. 5. When the device illustrated in FIG. 2 begins operation in step 501, the AC voltage is set in step 502 by the power controller 201 to zero (i.e., (VIAL In steps 503 and 504, at time t1 the timer 202 turns the power controller 201 ON (AC voltage ON), and waits for a predetermined period of time (essentially steps 503-507 in a loop until time t2). If during this time (step 505), plasma discharge was not detected by plasma detector 203, the AC voltage setting in step 506 will be increased (e.g., either during the time period t1-t2, or for the next cycle beginning with t3). The timer 202 may then turn the power controller 201 OFF in steps 507-508 at time t2 For a next cycle beginning with time t3 (return of process to step 503), when the power controller 201 is ON, the AC voltage will now be higher than in the previous cycle. This process repeats until the plasma discharge is ignited and detected by detector 203 in step 505 (e.g., corresponding to time 141, and any other subsequent instances of time when the AC voltage is ON). At this time, the AC voltage is high enough to ignite the plasma discharge.

When a plasma discharge is detected b detector 203, it sends a signal to the timer 202 (e.g., at time t4). In response, the tinier 202 turns the power controller 201 OFF (e.g., at time t4) in step 508, and the AC voltage setting remains the same for the next cycle. During a next cycle, when the power controller 201 is ON, the AC voltage will not change. As such, the process has become stable.

The timer 202 may turn the AC voltage ON, according to any repetition rate, including but not limited to a predetermined pulse width modulated frequency, and turn the AC voltage OFF, when plasma discharge is detected.

Figure 3:
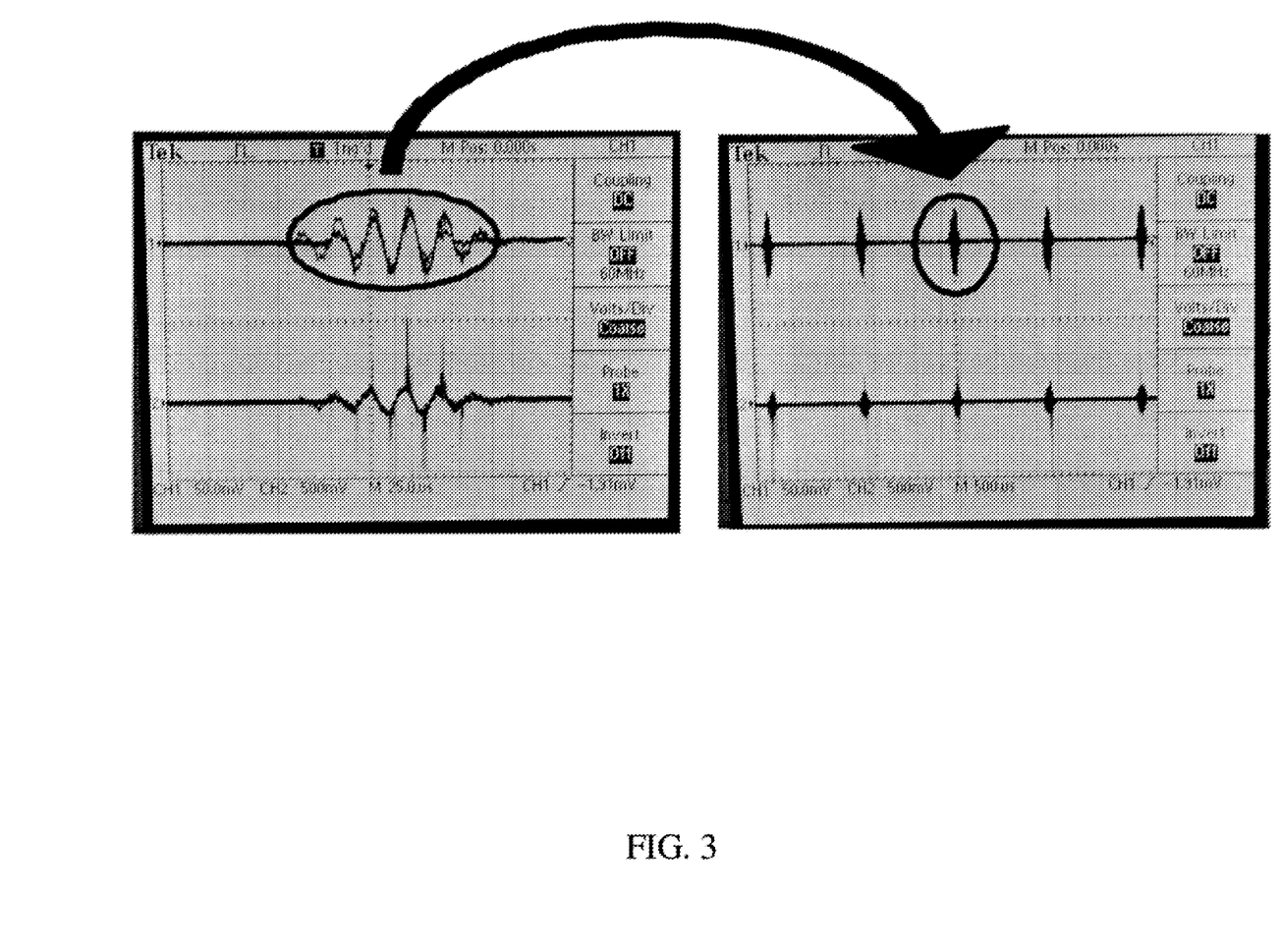
FIG. 3 shows exemplary oscilloscope images showing AC voltage frequency (left image) and pulse repetition rate (right image).

FIG. 3 shows an oscilloscope trace with an exemplary waveform for an AC driving voltage. The amount of ions produced by the ionizer may be adjusted by changing the Frequency of the AC voltage or the pulse repetition rate.

Figure 7A:
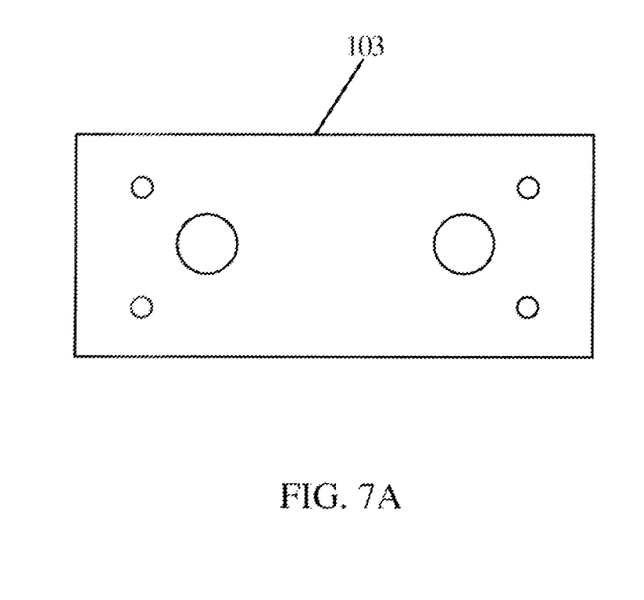
FIG. 7A illustrates a dielectric side of a substrate of an ionizer in accordance with embodiments of the present invention.
Figure 7B:
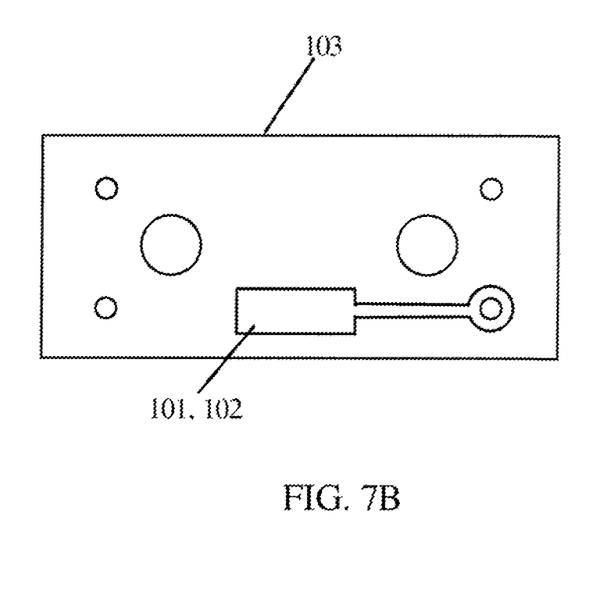
FIG. 7B illustrates an electrode side of a substrate of an ionizer in ac accordance with embodiments of the present invention.

Referring to FIGS. 7A-7B, in alternative embodiments, the ionizer plates may be made from alumina (e.g., approximately 1 mm thick) with electrodes 101, 102 printed with a conductor (e.g., Au/Pt). Spacers 105 may be from PIPE (e.g., 380 µm to 500 µm thick) to hold the two apart in the configuration of FIG. 1A. The spacers 105 form a channel to direct the gas flow through the ionizer 100 where the plasma is created before the ions are carried out of the ionization region, The gas is ionized when it is in a static, no flow state, but in a no flow case, the ionization creates a lot of ozone and $NO_x$ ions in air. Flowing the gas at approximately 300 seem (standard cubic centimeters per minute) to 500 sccm may be performed for an IMS application, but the ionizer works at more than approximately 1000 seem as well. The metallic electrode may be a printed metal pad of approximately 5 mm×3 mm with a lead to connect to the electronic drivers.

The plates may be made from alumina or another dielectric, such as glass or printed circuit board material. The metal electrode may be a printed or painted metallic ink, or a thicker metal structure, such as a metal tape, wire, or thin metal. The structure may also be a metal support for the electrode coated with as dielectric material. The shape of the electrodes does not need to be rectangular, but may be circular or another shape to conform to a specific application. FIG. 7A illustrates a dielectric side of the plates, while FIG. 7B illustrates a metal electrode side of the plates.

By protecting the electrodes with a ceramic or dielectric, an ionizer will have a longer lifetime and will generate a cleaner plasma.

What is claimed is:

1. A method for operating an ionizer, comprising:
   performing a plurality of cycles of switching on and off, according to a predetermined repetition rate, an alternating current ("AC") voltage output from a power controller applied to electrode plates of the ionizer; and
   prematurely interrupting the application of the AC voltage from the power controller to the electrode plates of the ionizer when a plasma discharge is detected between the electrode plates of the ionizer.

2. The method as recited in claim 1, wherein the prematurely interrupting of the application of the AC voltage from the power controller to the electrode plates of the ionizer when the plasma discharge is detected between the electrode plates of the ionizer occurs when the AC voltage is switched on from the power controller to the electrode plates of the ionizer.

3. The method as recited in claim 1, wherein the prematurely interrupting of the application of the AC voltage from the power controller to the electrode plates of the ionizer when the plasma discharge is detected between the electrode plates of the ionizer includes turning off the AC voltage that switched on from the power controller to the electrode plates of the ionizer.

4. The method as recited in claim 1, further comprising switching on the AC voltage from the power controller to the electrode plates of the ionizer subsequent to the premature interruption of the application of the AC voltage from the power controller to the electrode plates of the ionizer when the plasma discharge is detected between the electrode plates of the ionizer.

5. The method as recited in claim 1, further comprising a differential mobility spectroscopy ("DMS") analyzer coupled to the ionizer in a manner so that the DMS analyzer receives the ionized gas from the ionizer, wherein the ionizer includes a non-radioactive ionization source for ionizing a gas flowing between the electrode plates of the ionizer.

6. The method as recited in claim 1, wherein a first one of the electrode plates of the ionizer receives the AC voltage, and wherein a second one of the electrode plates is electrically connected to a ground potential, wherein a gas being ionized by the ionizer flows between the first and second electrode plates.

7. The method as recited in claim 6, wherein the AC voltage is applied across the first and second electrode plates.

8. The method as recited in claim 7, wherein the first and second electrode plates are electrically isolated from each other.

9. The method as recited in claim 6, further comprising:
a first dielectric material coated on the first electrode plate in a manner so that the first dielectric material prevents contact between the first electrode plate and the gas being ionized; and
a second dielectric material coated on the second electrode plate in a manner so that the second dielectric material prevents contact between the second electrode plate and the gas being ionized.

10. A system for operating an ionizer, comprising:
a power controller suitable for outputting an AC voltage to electrode plates of the ionizer;
a timer suitable for switching on and off, according to a predetermined repetition rate, the AC voltage output from the power controller to the electrode plates of the ionizer; and
a detector coupled to the ionizer suitable for detecting an occurrence of a plasma discharge between the electrode plates of the ionizer;
the timer suitable for prematurely switching off the AC voltage from the power controller to the electrode plates of the ionizer in response to the detector detecting the plasma discharge between the electrode plates of the ionizer.

11. The system as recited in claim 10, wherein the prematurely switching off the AC voltage from the power controller to the electrode plates of the ionizer in response to the detector detecting the plasma discharge between the electrode plates of the ionizer occurs when the AC voltage is switched on from the power controller to the electrode plates of the ionizer.

12. The system as recited in claim 10, further comprising the timer suitable for switching on the AC voltage from the power controller to the electrode plates of the ionizer subsequent to the premature switching off the AC voltage from the power controller to the electrode plates of the ionizer in response to the detector detecting the plasma discharge between the electrode plates of the ionizer.

13. The system as recited in claim 10, further comprising a differential mobility spectroscopy ("DMS") analyzer coupled to the ionizer in a manner so that the DMS analyzer receives the ionized gas from the ionizer, wherein the ionizer includes a non-radioactive ionization source for ionizing a gas flowing between the electrode plates of the ionizer.

14. The system as recited in claim 10, wherein the detector monitors a current flowing through the electrode plates to detect the occurrence of the plasma discharge.

15. The system as recited in claim 10, wherein a first one of the electrode plates of the ionizer receives the AC voltage, and wherein a second one of the electrode plates is coupled to a ground potential, wherein a gas being ionized by the ionizer flows between the first and second electrode plates.

16. The system as recited in claim 10, further comprising:
a dielectric material coated on the electrode plates in a configuration so that the dielectric material prevents contact between the electrode plates and the gas being ionized.

17. A method for driving power applied to an ionizer, comprising:
(a) switching on the power applied to the electrodes of the ionizer for a first predetermined time period, wherein a first one of the electrodes of the ionizer receives an AC voltage when the power is applied to the electrodes, and wherein a second one of the electrodes is coupled to a ground potential;
(b) determining if a plasma discharge has occurred during the first predetermined time period;
(c) if the plasma discharge has occurred during the first predetermined time period, then switching off the power applied to the electrodes of the ionizer;
(d) switching off the power applied to the electrodes of the ionizer for a second predetermined time period regardless whether the plasma discharge has occurred during the first predetermined time period; and
(e) repeating steps (a)-(d).

18. The method as recited in claim 17, further comprising a differential mobility spectroscopy ("DMS") analyzer coupled to the ionizer in a manner so that the DMS analyzer receives the ionized gas from the ionizer, wherein the ionizer includes a non-radioactive ionization source for ionizing a gas flowing between the electrode plates of the ionizer.

19. The method as recited in claim 17, wherein the ionizer includes a radioactive ionization source for ionizing a gas flowing between the electrode plates of the ionizer.

20. The method as recited in claim 17, wherein a gas being ionized by the ionizer flows between the first and second electrodes, wherein the first and second electrodes are electrically isolated from each other.

21. The method as recited in claim 20, further comprising:
a first dielectric material coating the first electrode in a configuration that prevents contact between the first electrode and the gas being ionized; and
a second dielectric material coating the second electrode in a configuration that prevents contact between the second electrode and the gas being ionized.

22. The method as recited in claim 20, further comprising increasing a magnitude of the AC voltage during step (e) if the plasma discharge has not occurred during the first predetermined time period.

\* \* \* \* \*